(12) United States Patent
Spitznagel

(10) Patent No.: US 10,716,588 B2
(45) Date of Patent: Jul. 21, 2020

(54) SURGICAL INSTRUMENT

(71) Applicant: KARL KLAPPENECKER GMBH & CO. KG, Tuttlingen-Nendingen (DE)

(72) Inventor: Bernhard Spitznagel, Seitingen-Oberflacht (DE)

(73) Assignee: KARL KLAPPENECKER GMBH & CO. KG, Tuttlingen-Nendingen (DE)

( * ) Notice: Subject to any disclaimer, the term of this patent is extended or adjusted under 35 U.S.C. 154(b) by 198 days.

(21) Appl. No.: 14/775,036

(22) PCT Filed: Mar. 12, 2014

(86) PCT No.: PCT/EP2014/054838
§ 371 (c)(1),
(2) Date: Nov. 20, 2015

(87) PCT Pub. No.: WO2014/140100
PCT Pub. Date: Sep. 18, 2014

(65) Prior Publication Data
US 2016/0174997 A1 Jun. 23, 2016

(30) Foreign Application Priority Data
Mar. 15, 2013 (DE) .................. 10 2013 102 679

(51) Int. Cl.
*A61B 17/28* (2006.01)
*A61B 17/88* (2006.01)
*A61B 17/16* (2006.01)
*A61B 90/00* (2016.01)
*A61B 17/00* (2006.01)

(52) U.S. Cl.
CPC ...... *A61B 17/2841* (2013.01); *A61B 17/1611* (2013.01); *A61B 17/8863* (2013.01); *A61B 2017/0046* (2013.01); *A61B 2017/00424* (2013.01); *A61B 2017/2845* (2013.01); *A61B 2090/0813* (2016.02)

(58) Field of Classification Search
CPC ......................... A61B 17/1611; A61B 17/8863
USPC .......................................................... 606/1
See application file for complete search history.

(56) References Cited

U.S. PATENT DOCUMENTS

| | | | | |
|---|---|---|---|---|
| 2,427,169 A | * | 9/1947 | Wandel | A61B 17/12009 606/139 |
| 5,483,952 A | * | 1/1996 | Aranyi | A61B 17/2909 600/131 |
| 5,964,756 A | * | 10/1999 | McGaffigan | A61B 18/1485 604/22 |
| 2006/0116706 A1 | * | 6/2006 | Martin | A61B 17/1611 606/184 |

FOREIGN PATENT DOCUMENTS

| | | |
|---|---|---|
| DE | 19948031 A1 | 5/2001 |
| DE | 102010013296 A1 | 9/2011 |
| EP | 0534303 A2 | 3/1993 |

OTHER PUBLICATIONS

International Search Report for PCT/EP2014/054838 dated Jan. 23, 2015.

* cited by examiner

*Primary Examiner* — Aaron F Roane
(74) *Attorney, Agent, or Firm* — Bachman and LaPointe PC; George Coury

(57) ABSTRACT

A surgical instrument comprising a shaft (1) on which a first handle (3) is formed, a pushing part (2) which is actuated by a second handle (4), and a force accumulator for returning the pushing part (2), wherein the force accumulator and the pushing part (2) are integrally formed.

15 Claims, 5 Drawing Sheets

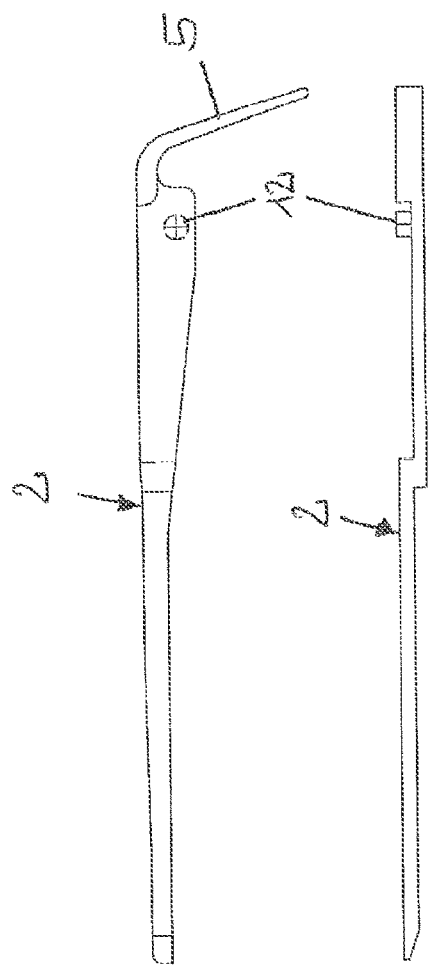

SURGICAL INSTRUMENT

BACKGROUND OF THE INVENTION

The present invention relates to a surgical instrument.

A great many surgical instruments are known from the prior art, for example forceps, retractors, clamps, bows, dilators and scissors, in a wide variety of designs and for many different surgical uses.

Surgical instruments are preferably shaped ergonomically and are able to be operated with one hand by an operator.

Surgical instruments of these kinds often have a spring, such that the operator moves the instrument in one direction by applying a certain force, and the opposite movement, i.e. the movement back to a starting position, is effected by a restoring force of the spring.

In the field of surgical instruments, particularly in the field of medical devices in general, an increasing problem in recent times has surrounded the cleaning of often complex devices. As the devices become ever more technically refined, greater effort is required to clean them.

In particular, an immense risk is posed here by the partial regions of medical devices that cannot be sterilized by means of a cleaning process, in particular using cleaning agents.

The problem addressed by the present invention is that of overcoming the disadvantages of the prior art. In particular, a device is to be made available which can be easily dismantled into individual parts and can likewise be easily assembled and which can be easily cleaned in a cleaning process in such a way that it is sterile.

SUMMARY OF THE INVENTION

The problem is solved by the features of a surgical instrument, comprising a shaft, on which a first handle is formed; a sliding part, which can be actuated by a second handle, and a force accumulator for returning the sliding part, wherein the force accumulator and the sliding part are integrally formed.

The surgical instrument according to the invention is preferably a sliding shaft instrument that can have various functional elements. The functional element is the element actuated by the sliding shaft instrument, wherein forceps or cutting elements are preferably used as functional elements.

An illustrative embodiment of a surgical instrument according to the invention is a litz wire cutter.

The connection between shaft and sliding part is preferably effected via rails or grooves. All guides are open, there are no dead spaces or sharp corners/angles. Moreover, in this way, no joins are present. In the surgical instrument according to the invention, there is no need for screws, rivets, welds or the like. There is therefore also no danger of corrosion.

It is important in this context that, on the one hand, the sliding part can be pushed onto the shaft horizontally by movement of a second handle and that, on the other hand, the sliding part can be released from the shaft. The sliding part can preferably be pushed into the shaft from behind, i.e. from the proximal direction.

A first handle is formed on the shaft. This first handle is operatively connected to the second handle. The second handle is connected pivotably to the shaft. Moreover, the sliding part can be actuated by the second handle. This means that the sliding part can be moved relative to the shaft by pulling the second handle to the first handle. Moreover, a force accumulator for returning the sliding part is present on the shaft. The return is such that the second handle is returned to its starting position and, by manual actuation, can or must be pulled back to the first handle. It is advantageous here that the surgical instrument can be dismantled and assembled without using tools.

The special aspect according to the invention is that the force accumulator and the sliding part are integrally formed. The configuration of the integral formation is significant only insofar as the chosen configuration must enable the sliding part to be returned to the shaft. For this purpose, a contact point between the force accumulator and the shaft is generally needed, the contact point serving as a force anchor. It is once again advantageous here that the integral formation of the force accumulator with the shaft ensures that no dead surface areas are present, which permits simple sterilization. This is especially so given that any component parts otherwise used, for example leaf springs, can be sterilized only with difficulty.

Moreover, the second handle has a holding area at one end. This holding area comprises finger depressions. These finger depressions serve for better and easier manipulation of the surgical instrument. They increase the degree of user friendliness and safety.

The second handle has, at the other end, a recess for coupling to the sliding part. The recess can be provided either in the form of a hole, an opening or a depression. The important point is that the second handle can be pivotably connected to the sliding part.

The second handle forms a hook-in pin. This hook-in pin serves for coupling to the shaft. In a preferred illustrative embodiment, the hook-in pin is non-circular. The hook-in pin is intended to permit a likewise pivotable connection to the shaft. The non-circular configuration of the hook-in pin, in conjunction with a hook-in recess of the shaft, prevents accidental incorrect insertion of the second handle into the shaft.

One illustrative embodiment moreover has, in the area of the hook-in recess, a passage in the shaft. This passage is shaped in such a way that the second handle protrudes into the shaft in such a way that the recess of the second handle can be coupled to the sliding part located in the shaft. Specifically, the second handle is pushed into the hook-in recess. The area of the second handle that has the opening is pushed with the aid of the passage into the interior of shaft and sliding part. The sliding part in turn has a stub that can be introduced into the recess.

In a particularly preferred illustrative embodiment, the force accumulator is a bow formed integrally at one end on the sliding part. The bow is operatively connected to a limit stop of the shaft, wherein the bow returns the second handle from the first handle. The shape, size and formation of the bow and of the limit stop are dependent on the area of use of the surgical instrument and of the functional element used. For example, the bow can also be configured with a semicircular shape or with reinforcing ribs or the like. The spring is preferably formed integrally with one of the components. However, it could also be integrated separately in the device.

The surgical instrument can be dismantled by the following steps:

the sliding part is pressed laterally away from the shaft,
the second handle is pulled from the shaft, and
the released sliding part is removed from the shaft.

The surgical instrument according to the invention is produced by the following steps among others:

openings and slits are introduced by means of a side milling cutter,
undercuts and grooves are formed by machining.

BRIEF DESCRIPTION OF THE DRAWINGS

Further advantages, features and details of the invention are set forth in the following description of preferred illustrative embodiments and in the drawings, in which:

FIG. 3 shows a side view of a first part of a litz wire cutter according to the invention;

FIG. 4 shows a plan view of the part according to FIG. 3;

DETAILED DESCRIPTION

Figure 1:
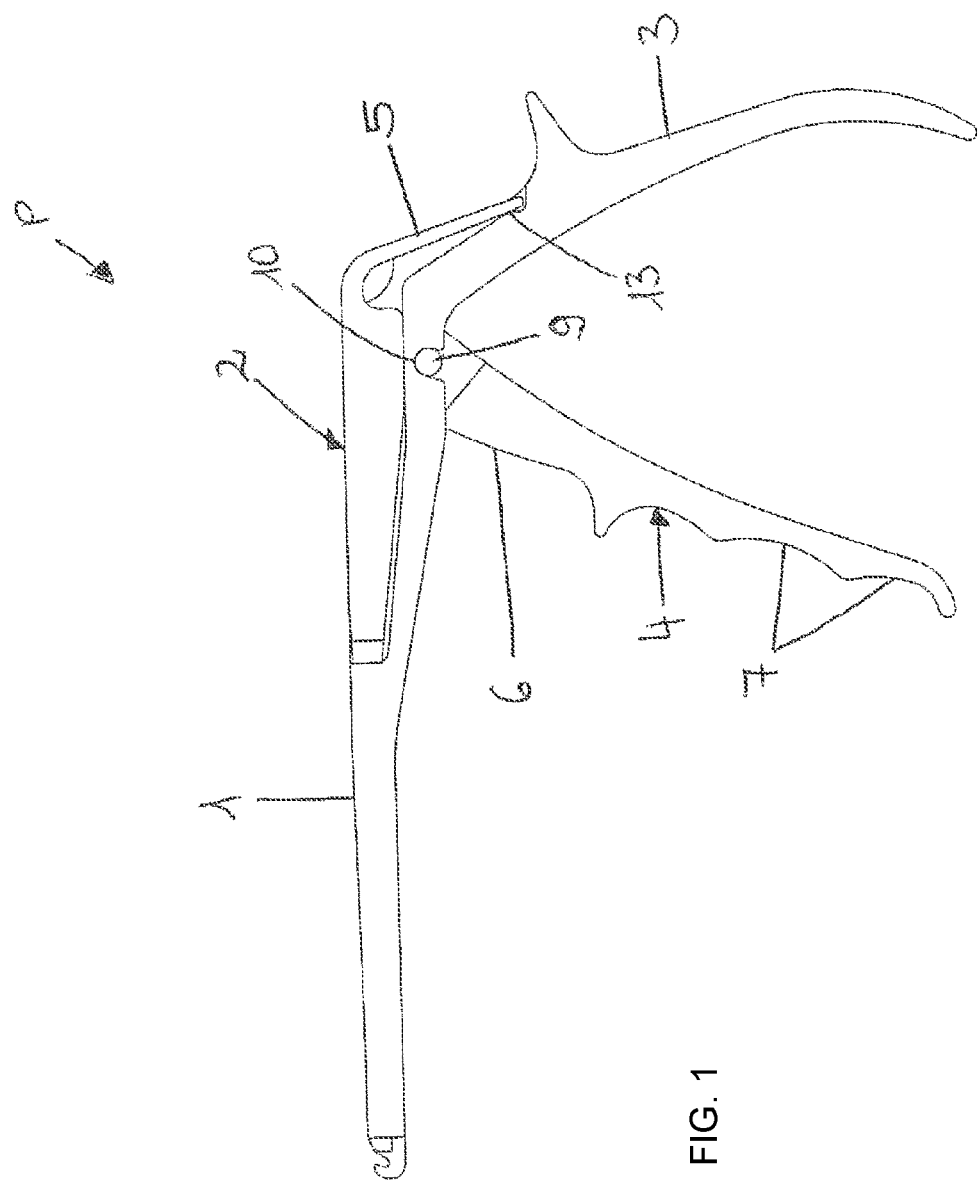
FIG. 1 shows a side view of a litz wire cutter according to the invention.

A litz wire cutter P is shown in the position of use in a side view in FIG. 1. The litz wire cutter P is composed of a shaft 1, on which a first handle 3 is integrally formed.

A sliding part 2 is also present. The figure shows the sliding part 2 pushed into the shaft 1.

A second handle 4 is also shown. At one end, the second handle 4 has a holding area 6. The holding area 6 in turn consists in part of finger depressions 7.

A bow 5 is formed integrally on one end of the sliding part 2. The bow 5 protrudes substantially at right angles from the sliding part 2.

Figure 2:
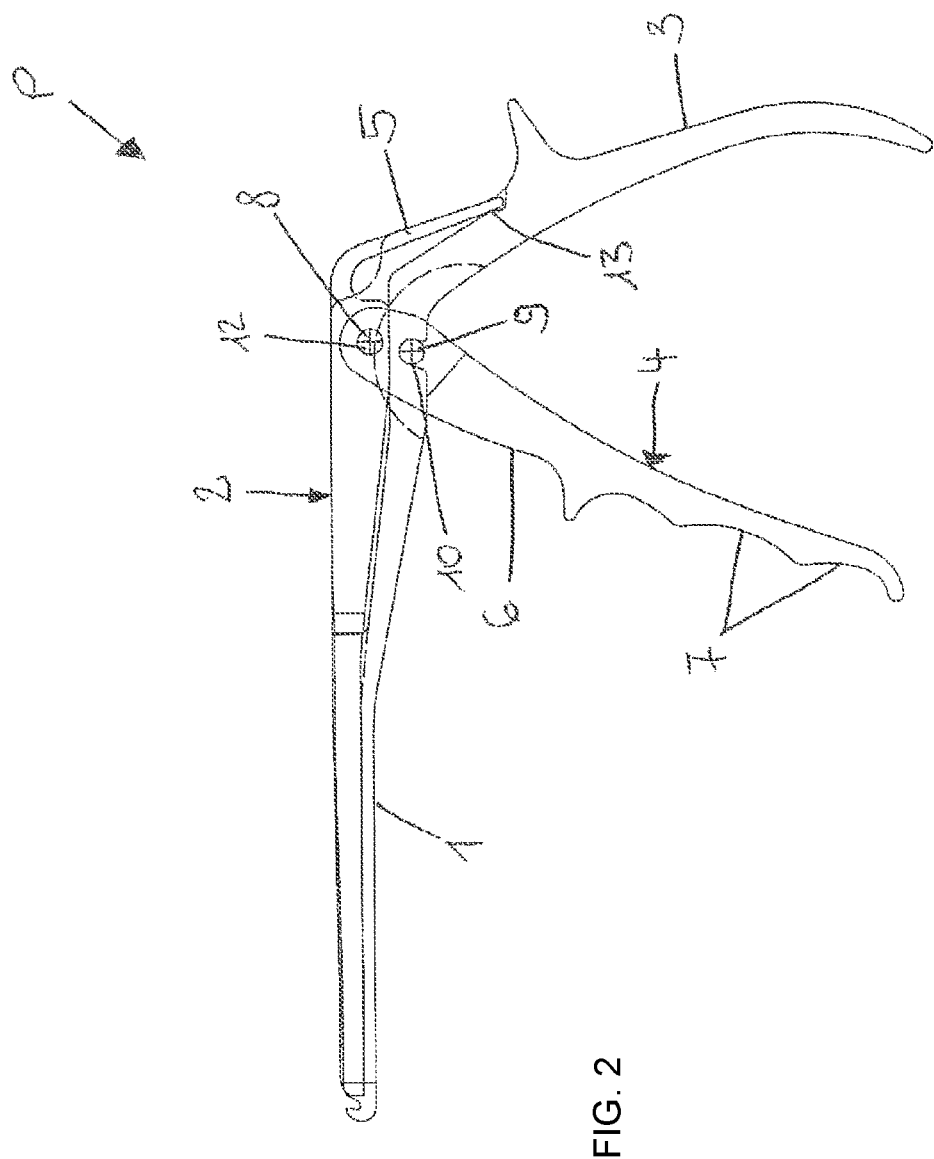
FIG. 2 shows a side view of a litz wire cutter according to the invention.

The second handle 4 has, at the other end, a recess 8 for coupling to the sliding part 2, which recess 8 can be seen better in FIG. 2.

In addition, the second handle 4 has a hook-in pin 9 for coupling to the shaft 1. The hook-in pin 9 is shown pushed into a hook-in recess 10 of the shaft 1.

In the area of the hook-in recess 10, a passage 11 is present in the shaft 1. This passage 11 can be seen particularly clearly in FIG. 6. The second handle 4 protrudes into the shaft 1 in such a way that the recess 8 can be coupled to the sliding part 2 located in the shaft 1. The coupling of the second handle 4 is effected by the sliding part 2 having a stub 12 that can be introduced into the recess 8. The configuration of the stub 12 can be seen particularly clearly in FIGS. 3 and 4.

The sliding part 2 is shown in a side view in FIG. 3. A cutting edge (not indicated) is present at the other end from the bow 5. FIG. 4 shows that the sliding part 2 is configured in the shape of a question mark, wherein the stub 12 is formed in a recessed area of the sliding part 2.

Figures 5, 6:
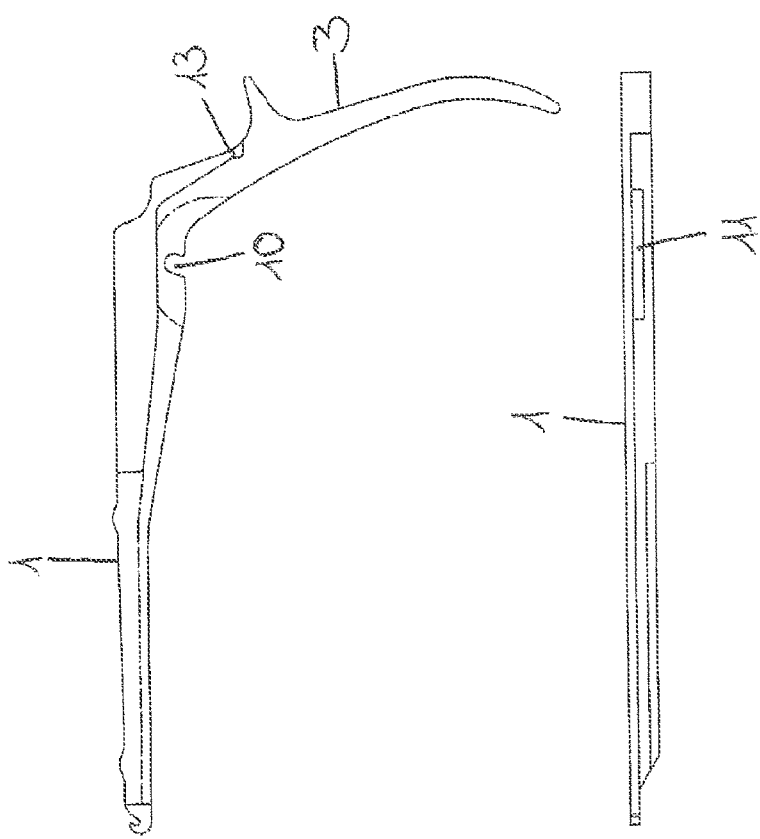
FIG. 5 shows a side view of a second part of a litz wire cutter according to the invention.
FIG. 6 shows a plan view of the part according to FIG. 5.

FIG. 5 shows a side view of the shaft 1. A limit stop 13 is present at the transition between the area of the hook-in recess 10 and the first handle 3. The limit stop 13 serves as force anchor for the bow 5 of the sliding part 2.

In addition to the passage 11 present in the area of the hook-in recess 10, FIG. 6 also shows how the shaft 1 is configured as a U-shaped profile approximately over a third of its surface area. The configuration as a U-shaped profile allows the sliding part 2 to be mounted with better mobility while still being stable.

Figure 7:
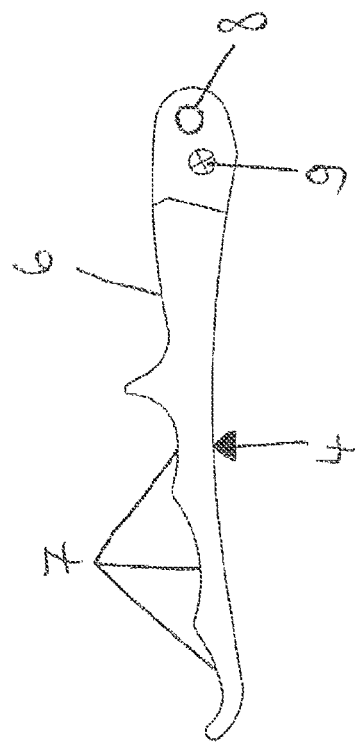
FIG. 7 shows a side view of a further part of a litz wire cutter according to the invention.

FIG. 7 shows how the opening 8 introduced at the end is formed on the second handle 4. From the opening 8 toward the finger depressions 7, the hook-in pin 9 is once again shown.

The invention claimed is:

1. A surgical instrument, comprising:
a shaft (1) on which a first handle (3) is formed;
a sliding part (2) which is actuated by a second handle (4) to move from a first position to a second position; and
a force accumulator for returning the sliding part (2) to the first position, wherein the force accumulator is a bow (5) formed integrally at one end on the sliding part (2), wherein the bow (5) and the second sliding part (2) are a single piece such that there are no dead spaces.

2. The surgical instrument as claimed in claim 1, wherein the second handle (4) has a holding area (6) at one end.

3. The surgical instrument as claimed in claim 2, wherein the holding area (6) comprises finger depressions (7).

4. The surgical instrument as claimed in claim 2, wherein the second handle (4) has, at the other end, a recess (8) for coupling to the sliding part (2).

5. The surgical instrument as claimed in claim 1, wherein the second handle (4) forms a hook-in pin (9) for coupling to the shaft (1).

6. The surgical instrument as claimed in claim 5, wherein the hook-in pin (9) is non-circular.

7. The surgical instrument as claimed in claim 6, wherein the sliding part (2) has a stub (12), which is introduced into the recess (8).

8. The surgical instrument as claimed in claim 5, wherein the shaft (1) has a hook-in recess (10) for receiving the hook-in pin (9).

9. The surgical instrument as claimed in claim 8, wherein, in the area of the hook-in recess (10), a passage (11) is present in the shaft (1), such that the second handle (4) protrudes into the shaft (1) in such a way that the recess (8) can be coupled to the sliding part (2) located in the shaft (1).

10. The surgical instrument as claimed in claim 1, wherein the bow (5) is operatively connected to a limit stop (13) on the shaft (1), wherein the bow (5) returns the second handle (4) away from the first handle (3).

11. The surgical instrument as claimed in claim 1, wherein the first handle (3) has a limit stop (13), and wherein the bow (5) terminates in an end which engages with limit stop (13).

12. A method for dismantling a surgical instrument comprising a shaft (1) on which a first handle (3) is formed; a sliding part (2) which is actuated by a second handle (4) to move from a first position to a second position; and a force accumulator comprising a bow (5) formed integrally at one end on the sliding part (2) for returning the sliding part (2) to the first position, wherein the bow (5) and the second sliding part (2) are a single piece such that there are no dead spaces, comprising the following steps:
laterally pressing away the sliding part (2) from the shaft (1);
pulling the second handle (4) from the shaft (1); and
removing the released sliding part (2) from the shaft (1).

13. A surgical instrument, comprising:
a first piece having a shaft (1) on which a first handle (3) is formed;
a second piece having a sliding part (2) which is movable relative to the shaft (1) between a first position and a second position, and having a force accumulator for returning the sliding part (2) relative to the shaft (1) from the second position to the first position, wherein the force accumulator is a bow (5) formed integrally at one end of the sliding part (2), wherein the bow (5) and the second sliding part (2) are a single piece such that there are no dead spaces; and
a third piece having a second handle (4) which is movable relative to the first handle (3) and which is engaged with the first piece and the second piece to move the sliding part (2) from the first position to the second position when the second handle (4) is moved toward the first handle (3), and wherein the third piece engages the first piece and the second piece to hold the first piece, the second piece and the third piece together.

14. The surgical instrument as claimed in claim 13, wherein releasing the third piece from the second piece allows the first piece, the second piece, and the third piece to be separated from each other.

15. The surgical instrument as claimed in claim 13, wherein the sliding part (2) and the bow (5) are a single piece part with no mechanical fasteners or joins there between.

* * * * *